United States Patent [19]

Callot

[11] Patent Number: 5,318,678
[45] Date of Patent: Jun. 7, 1994

[54] METHOD AND APPARATUS FOR ANALYZING THE STATE OF PROTECTION AGAINST CORROSION OF A WORK UNDER CATHODIC PROTECTION

[75] Inventor: Pierre Callot, Mulhouse, France

[73] Assignee: Gaz de France (Service National), Paris, France

[21] Appl. No.: 813,442

[22] Filed: Dec. 26, 1991

[30] Foreign Application Priority Data

Dec. 31, 1990 [FR] France .................. 90 16551

[51] Int. Cl.$^5$ .................................... C23F 13/04
[52] U.S. Cl. ........................ 204/153.11; 204/147; 204/196
[58] Field of Search .............. 204/147, 153.11, 196, 204/404

[56] References Cited

U.S. PATENT DOCUMENTS

| | | | |
|---|---|---|---|
| 4,080,272 | 3/1978 | Ferry et al. | 204/147 |
| 4,080,565 | 3/1978 | Polak et al. | 204/153.11 |
| 4,138,323 | 2/1979 | Statsenko et al. | 204/147 |
| 4,395,318 | 7/1983 | Tait et al. | 204/153.11 |
| 4,591,792 | 5/1986 | Birchmeier et al. | 324/425 |
| 4,658,365 | 4/1987 | Syrett et al. | 204/147 |

OTHER PUBLICATIONS

Chen, Chi-Tsong, "System And Signal Analysis", New York, 1989, Saunders College Publishing, pp. 164-166 and 314-317.
Extended Abstracts, vol. 84, No. 2, Oct. 1984, Princeton, N.J., p. 265, D. Britz, "The Use of a Computer in the Corrosion Laboratory".
Electrochem. Corrosion Testing, F. Mansfeld, et al. EDS 1981, pp. 110-149; "Electrochem. Impedance Techniques..." D. D. MacDonald, et al., pp. 139, 1.10, 140.
Journal of the Electrochemical Society, vol. 130, No. 12, Dec. 1983, Manchester, N.H., pp. 2329-2334, M. Rosen, et al. "Tafel Constants and Changes in Hydrogen...".

Primary Examiner—John Niebling
Assistant Examiner—Kishor Mayekar

[57] ABSTRACT

A study is made of the changeover time of the voltage between an electrode and a metal work piece buried in the ground and protected against corrosion by an electric current. For this study, it is intended momentarily to interrupt the circulation of the protective current, to read the voltage between the work piece and the electrode, to pass these readings to an analog filter, to smooth these filtered signals by substituting them with values corresponding to a continuous and monotonic postulated function, and then to mathematically reconstruct the change in the voltage signals between the work piece and electrode such as it would be without filtering.

9 Claims, 2 Drawing Sheets

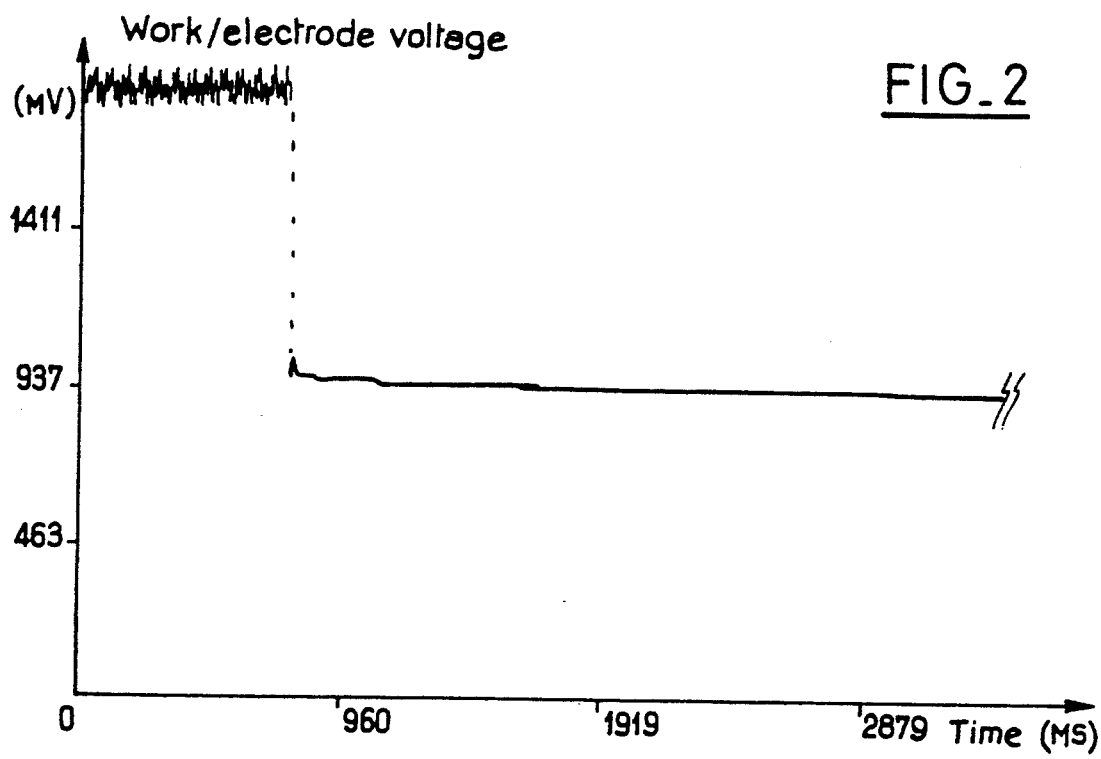
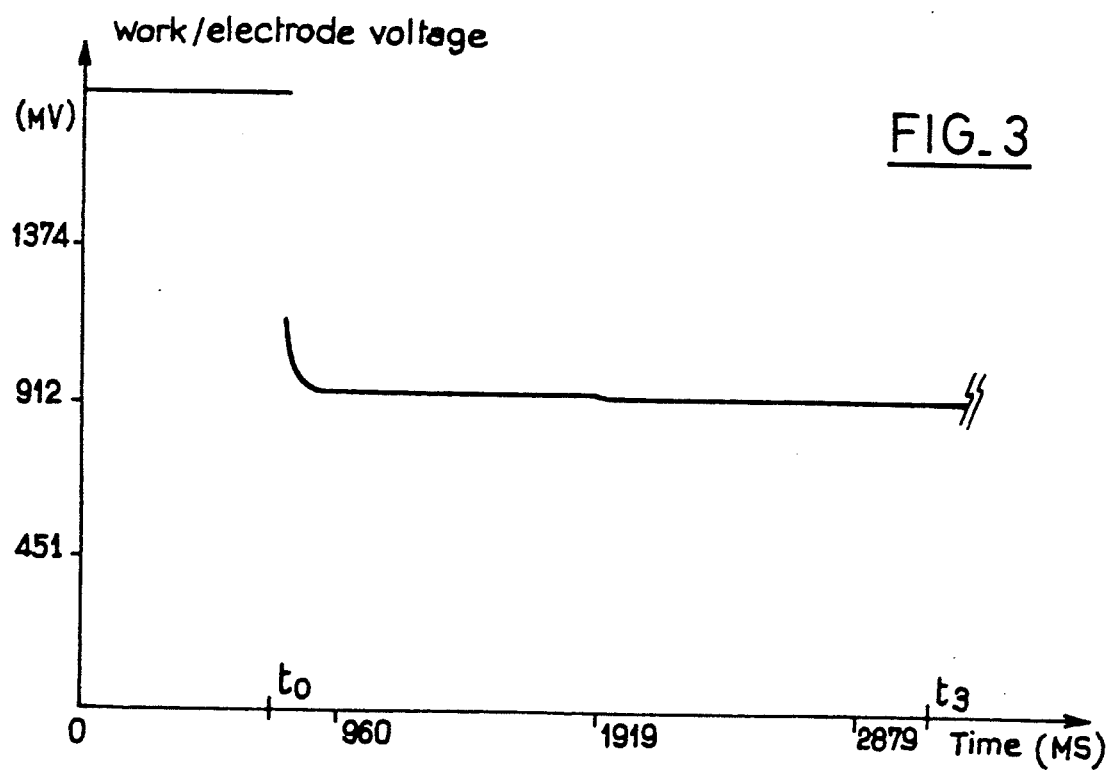

METHOD AND APPARATUS FOR ANALYZING THE STATE OF PROTECTION AGAINST CORROSION OF A WORK UNDER CATHODIC PROTECTION

FIELD OF INVENTION

The invention relates to a method of estimating the state of protection against corrosion of a metal work in contact with an electrolytic medium and normally protected cathodically or anodically against this corrosion by an imposed circulation of current between the work and a piece forming a counter-electrode, in contact with this medium.

BACKGROUND OF THE INVENTION

Cathodic protection is the most widespread. To provide this protection a circulation of electric current is usually created between the metal work and the solution surrounding it, a circulation such that the direction of the current flows from the solution to the metal, thus promoting the cathodic reaction in the region of the work to be protected, while transferring the oxidation reaction to the counter-electrode, thus forming an anode.

There are also cases in which the work forms an anode and the counter-electrode a cathode, (protection of certain metals, such as aluminium, which can be passivated in the electrolyte, via an "anodic protection" current).

Be that as it may, when a "cathodic" or "anodic" protection is applied to a work in contact with the ground (or another electrolytic medium) the effectiveness of the protection is usually measured by the value of the potential difference between the work and the electrolyte.

In actual fact, this voltage is measured between the metal of the protected work and a so-called "reference" complementary electrode in contact with the electrolyte. In practice, it is preferable to place this reference electrode some distance from the surface presumed to be protected.

The measurement of this voltage therefore includes a term due to the potential gradient in the ground.

Knowledge of the real metal/ground potential requires this undesirable term to be eliminated from the measurements.

A means usually used for this purpose consists in measuring this potential, after momentarily cutting the imposed protective current. A method which numerous practitioners have gone over to consists in cutting the protective current for about 3 seconds, the measurement(s) being made between 2 and 3 seconds after cutoff, and in then re-establishing the protective current for about 30 seconds, before a new cutoff.

It is therefore known nowadays that in order to check in particular the state of immunity as regards corrosion of a buried metal work, measurements must be made of potential of the work relative to the ground, protective current cut off, in order to eliminate from the measurement in particular the ohmic drop due to the flow of the current into the ground. Cancellation of this drop is in practice done in less than about one millisecond at the time of cutoff. It can therefore be considered as practically instantaneous.

When the work goes from the "under imposed protective current" situation to the zero current situation, a modification also occurs in the potential of the work relative to the ground. This modification is considered to be due to electrochemical phenomena occurring essentially at the interface between the metal and the ground.

Knowledge of the potential jump which occurs at the moment of cutting of the protective current makes it possible to know what the actual potential was in the situation of active protection of the work.

Quantitative knowledge of the amplitudes and rates of change immediately after cutoff makes it possible to determine what electrochemical phenomena are involved when the work, on leaving the protective situation, changes to a corrosion situation.

BRIEF DESCRIPTION OF THE INVENTION

The aim of the invention is to permit the acquisition and analysis of these phenomena.

However, in reality, an exhaustive and rigorous analysis of the parameters corresponding to an actual recorded situation is not possible.

It has therefore been necessary, in the invention, to simplify the problem by modelling.

A first simplification has been obtained by considering that, during the time interval in which the protective current is cut off, only one electrical phenomenon and two or three electrochemical phenomena can determine the form of the signal obtained.

A second simplification has been elicited from the observation that the principal chemical systems able to define the value of the potential between the metal of the work and the electrolyte are in an actual situation markedly differentiated in terms of potential and time constant.

For example, the values of potential of:

$$H^+ + e^- \rightarrow H$$

corresponding to the not-infinitely small "concentrations" of hydrogen, occupy values much lower than those of the system:

$$Fe^{++} + 2e^- \rightarrow Fe$$

capable of giving a degree of stability at the same potential.

Finally, the system:

$$\tfrac{1}{2}O_2 + 2e^- + H_2O \rightarrow 2OH^-$$

occupies even higher values.

Moreover, a third element has had to be taken into consideration in order to interpret the voltage measurements made.

In fact, the work/ground assembly constituting an electrical assembly which is frequently subject to electrical disturbances, invites the use of filters to attenuate the rapidly varying interference.

These filters unfortunately also deform the variations of electrical and electrochemical origin which follow cutoff.

According to the invention, these deformations have been eliminated by applying methods of filtering and processing the signal by modelling, the validity of which stems from properties particular to the phenomenon studied.

Electrically and electrochemically, the model adopted for the metal of the work/ground system should, after cutoff, always change in the same direction, any oscillatory phenomenon being excluded to the scale of a millisecond.

In practice, it has therefore been envisaged that the time-dependent potential signals would thus be subject to sampling and analogue filtering, and then smoothing by mathematical calculation, enabling practically all oscillatory phenomena to be eliminated.

In fact, an important aspect of the invention consists in that a monotonic and continuous electro-chemical change (without any singular point or point of inflection) has been postulated following the jump caused by cutting the protective current.

This postulate can be justified theoretically through the conditions of irreversible thermodynamics governing the passage from one steady-state regime to another likewise steady-state regime not too distant from the first, and involving the same reactions.

More precisely, according to the invention, the model in question postulates a time-dependent change in potential consisting of a jump of ohmic type, preferably corrected by the electrical time constant specific to the work/ground assembly, followed by slower and slower phenomena of electrochemical origin.

However, it has been observed that practically all the electrochemical phenomena which can be envisaged in the environment under consideration, and which were reproduced in the laboratory with no electrical interference, lead to variations in potential which are best represented by functions consisting of sums of exponentials and of polynomials.

The following function has in particular proved to be an entirely suitable model.

$$V(t) = At + B + C_1 e^{-t/\tau_1} + C_2 e^{-t/\tau_2}$$

A, B, $C_1$, $C_2$, $\tau_1$, $\tau_2$, being constants such that:

A: ordinate at the origin $t_0$ (instant of cutoff) of the linear component,

B: slope of the linear component, $C_1$, $C_2$: amplitudes of the exponential components, $\tau_1$, $\tau_2$: time constants of the exponential components.

The variation in potential (and in particular the combination jump + sum of exponentials) unfortunately being, as indicated above, highly deformed in the rapidly changing portion by the indispensable filtering operation, a mathematical processing was moreover therefore conceived making it possible, after smoothing, to recover the form of the signal which, after convolution with the filter transfer function, gives the voltage signal actually recorded.

By postulating that the undeformed (therefore unfiltered) depolarization signal exhibits the form of the model presented above, it thus became possible:

to eliminate all residual interference not completely eliminated by the filter and to reconstruct a noiseless voltage signal. This involves the "identification" operation which is presented below, then to reconstruct the variation in potential which would have given, after passage through the said analogue filter, the signal obtained above (that is to say, if reference is made to the previous postulated function V(t), the correct values of the constants A, B, $C_1$, $C_2$, $\tau_1$, $\tau_2$ of this function). This involves the so-called "deconvolution" operation which is also presented below.

Before briefly describing what these two operations, "identification" and "deconvolution", consist of mathematically, the structure will quickly be presented of the apparatus used in the invention in particular to accomplish these two operations and thus enable the operator to obtain a picture of the electrochemical situation existing in reality between the metal of the work and the ground, at the moment of cutoff.

For this purpose, reference will be made to the attached drawings in which:

BRIEF DESCRIPTION OF THE FIGURES

FIGS. 2 and 3 illustrate two simulation results relating to work/electrode voltage signals, on the one hand unfiltered (FIG. 2) and on the other hand filtered (FIG. 3).

DETAILED DESCRIPTION OF THE INVENTION

Figure 1:
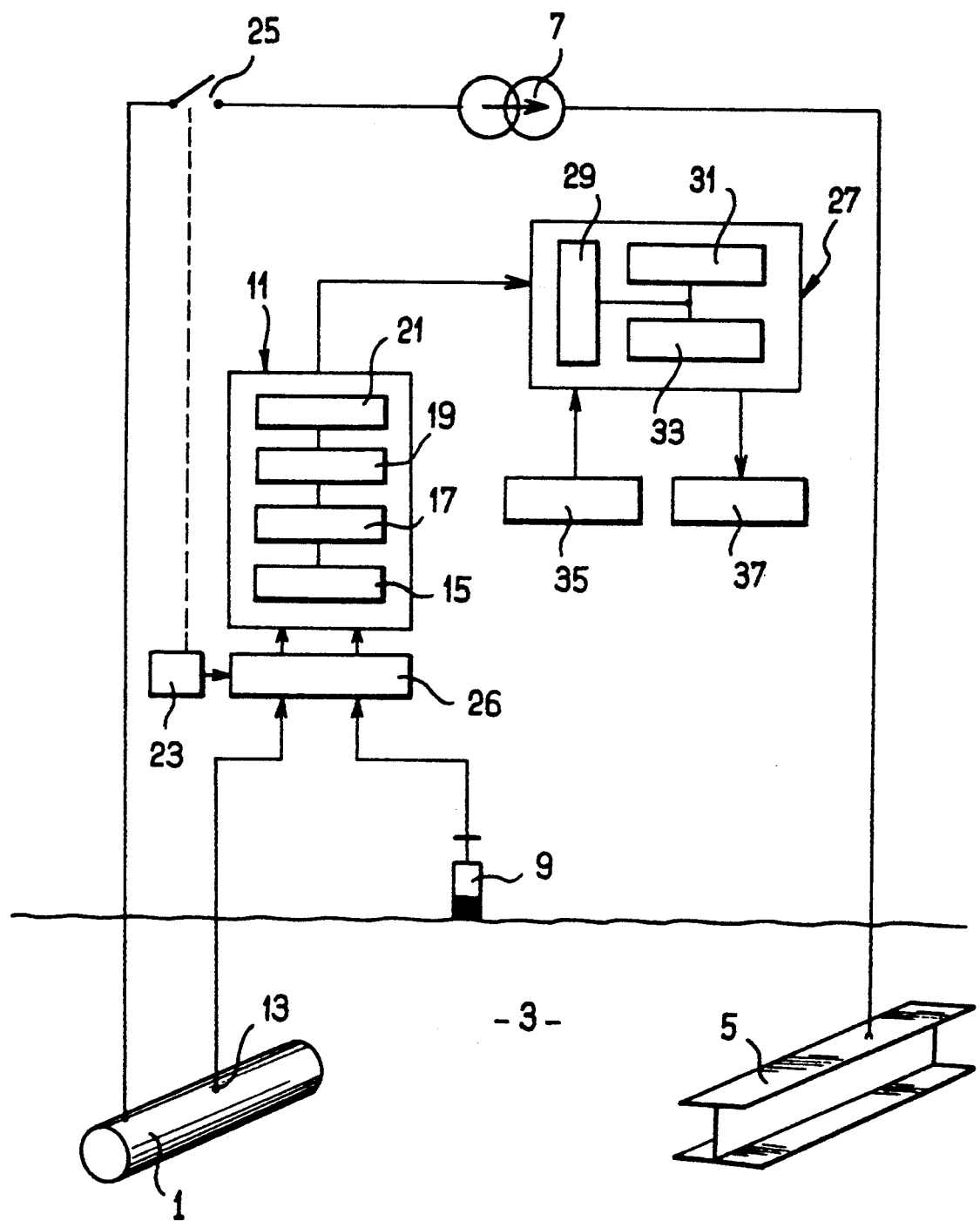
FIG. 1 is a block diagram showing an apparatus which can be used to implement the invention.

In what follows, only the case of "cathodic" protection will be discussed. However, the invention is also applicable to "anodic" protection mentioned above.

In FIG. 1, firstly, at 1 can be seen the metal pipe which in this example constitutes the electrically conducting work whose state of protection against corrosion it is desired to discover. This pipe 1 (possibly covered with a protective coating) is buried in the ground 3 which in the present instance constitutes the electrolytic medium. In this ground and relatively close by (for example a few tens of meters away) is also buried a piece or counter-electrode (here "anodic") 5 connected to the pipe by an electrical network in which a current circulates. In the chosen example, a current generator 7 delivers a constant, or a DC, current in the circuit such that the natural oxidation reaction is transferred to the piece 5, degeneration of which is accepted a priori.

It will be briefly noted that other types of cathodic protection exist nowadays, and in particular "by means of galvanic or sacrificial anode".

To measure the work/ground potential difference the electrode 9 is used, which, placed on the ground, acts as the reference electrode. It will, for example, possible for this electrode to be of the Cu/CuSO$_4$ or Ag/Ag Cl type.

To permit measurement and recording of the voltage between the pipe 1 and this electrode 9, an analogue filtering unit 11 has of course, furthermore been provided, the input of this unit being connected, via the measuring unit 26, to the electrode 9 as well as to the sensor 13 connected up to the metal of the work 1.

Preferably, the filtering unit 11 will comprise, after a differential amplifier 15, permitting the difference to be taken between the two signals emanating from the electrode 9 and sensor 13, two band rejectors 17, 19 as well as a low-pass filter 21, for example of second order.

During the trials which were undertaken, the band rejectors 17 and 19 were chosen to eliminate the 50 and 100 Hertz frequencies respectively, whereas the low-pass filter was chosen to eliminate all frequencies above 120 Hertz. But of course the choice of these frequencies will depend on the application adopted.

As is seen in FIG. 1, with the measuring unit 26 is also associated a clock 23 which can consist of a timeswitch, enabling the frequency of voltage measurement readings to be imposed, together with a contact or an interrupter 25 provided in the electrical circuit, connecting the pipe 1 to the anode piece 5 in order to interrupt and re-establish sequentially the circulation of the protective current imposed by the generator 7.

Once sampled and filtered, the "useful" voltage signals are next acquired and then processed in such a way that the operator can obtain the desired picture of the electrochemical situation existing between the metal and the ground before and slightly after cutting the protective current.

For this purpose, the calculator 27 comprises essentially an input/output board 29, a memory unit 31 and a microprocessor, which is associated with a calculation unit 33.

In practice, it will be possible for the board 29 to comprise at input a series of channels in direct mode or in differential mode, an analogue/digital (A/D) convertor, a sample-and-hold circuit, an analogue multiplexing system, and, at output, another series of channels with D/A conversion. A unit 35 (which can consist of a diskette unit associated with a controller, as well as a keyboard associated with its decoding board) and a viewing or display unit 37 (consisting, for example, of a screen and a printer with its associated controller) complete the assembly.

After this structural presentation of the means of the invention, the operations of "identification" and then of "deconvolution" will now be presented.

The Principle of Identification

This first step of processing the captured or acquired signals is of course executed in the calculator 27.

During this operation, it is desired to obtain a first approximation of the voltage parameters captured after cutoff, doing so by linearizing the various portions of the potential/time curve corresponding to the successive voltage readings.

In other words, here the captured signals are smoothed by substituting them with values corresponding to a continuous and monotonic postulated function having, as has been stated, advantageously the form $V(t) = A.t + B + C_1 e^{-t/\tau_1} + C_2 e^{-t/\tau_2}$ (the time origin being placed at the instant $t_0$ which corresponds of course to the moment of cutting of the protective current).

Example of an Identification Procedure

Let us assume, in connection with the figures, that the timeswitch 23 generates a control sequence of the order of 33 seconds in order to control the contact 25, this sequence also serving to synchronize the measuring apparatus 26. For 30 seconds, the contact 25 is closed (between 0 and $t_0$) and then open for the next 3 seconds (between $t_0$ and $t_3$). Whilst the contact 25 is closed, 512 reference points are sampled, whereas 2048 measurement points are captured with contact 25 open, these latter points constituting the essence of the phenomenon studied.

The first data supplied, corresponding to the 512 established protective current voltage measurements captured, firstly enable the calculation unit 33 to supply the actual established value of the voltage U between the work and the electrode when this current circulates, based on calculating the average value of this voltage, namely:

$$U = \sum_{i=0}^{512} V(i)/512$$

$V(i)$: voltage read with each measurement

After this, the computer first determines the constants A and B of the linear component of V(t).

With the exponential functions decreasing rapidly, it will be preferable to identify the parameters A and B from the experimental points situated in the interval lying between about 1.5 and 2 seconds following cutoff (namely $t_0 + 1.5$ s and $t_0 + 2$ s in FIG. 3).

The identification method used was that of the "least squares" method of approximation, known per se, which consists in attributing to a quantity by determined by a series of measurements, the value which minimizes the sum of the squares of the errors relative to a postulated function (in this particular case the function V(t)). For further details, reference can be made, for example, to the publication "least squares method" Y. Linnik—DUNOD—1963.

The constants $C_1$, $C_2$, $\tau_1$ and $\tau_2$ are next determined as follows:

For the sake of clarity, only the principle of calculation of the constants $C_1$ and $\tau_1$ will be presented below (this principle also being applicable to the constants $C_2$ and $\tau_2$).

Firstly, the linear component $At + B$ is subtracted from the curve recorded in the interval $t_0$ to $t_1$ (between 0 and 0.85 seconds following cutoff in the trial undertaken) i.e. $C_1 \times e^{-t/\tau_1} = V(t) - (At + B)$.

Next, take the Napierian logarithm of this value, i.e. $Ln(C_1) - t/\tau_1 = Ln[V(t) - (At + B)]$.

The tangential component is thus transformed into a straight line.

Then calculate the constants $Ln(C_1)$ and $(-1/\tau_1)$ by the method of least squares.

Deduce therefrom $C_1$ and $\tau_1$.

The "identified" values of A, B, $C_1$ and $\tau_1$, (indeed $C_2$, $\tau_2$), as well as the average voltage U before cutoff are therefore now stored in the memory, in the unit 31.

However, as stated earlier, the values of the constants of the exponential functions are intrinsically corrupted, incorporating within them the distortions due to the filtering unit 11.

The tables below show this indisputably.

TABLE 1

| | Simulation measurements before filtering (in this particular case only the values $C_1$ and $\tau_1$ have been considered) | | | | | |
|---|---|---|---|---|---|---|
| TRIALS | A(mV/s) | B(mV) | $C_1$(mV) | $\tau_1$(ms) | U | *Potential jump (mv) |
| 1 | −3 | 200 | 50 | 40 | 500 | 250 |
| 2 | −4 | 300 | 20 | 60 | 500 | 180 |
| 3 | −6 | 350 | 100 | 80 | 1050 | 550 |
| 4 | −10 | 800 | 200 | 100 | 1500 | 500 |

*The potential jump corresponds to U − (B + $C_1$).

TABLE 2

| | Measurements after passing through the filter | | | | | |
|---|---|---|---|---|---|---|
| TRIALS | A | B | $C_1$ | $\tau_1$ | U | Potential jump |
| 1 | −3 | 200 | 197 | 33 | 500 | 103 |
| 2 | −4 | 300 | 133 | 20 | 500 | 67 |
| 3 | −6 | 350 | 322 | 33 | 1000 | 328 |
| 4 | −10 | 800 | 396 | 58 | 1500 | 304 |

To remedy these variations originating from these constants which corrupt the results, consideration will now be given to reconstructing mathematically the change in the voltage signals, such as it would be without an analogue filter and with practically no interference.

This involves, as understood, the "deconvolution" operation.

Presentation of "Deconvolution"

During this operation, the postulated model V(t) will in practice be subjected to a series of convolutions with the filter transfer function which will previously have been recorded (for example, on the basis of a voltage pulse enabling the response of the unit 11 to this pulse to be stored).

Inside the calculator 27, the convolution, that is to say the result of each aforementioned convolution product, is next compared with the recorded signal.

By modifying, preferably gradually and simultaneously, the various parameters of the model, it will then be sought to minimize the mean square deviation between the model convolved with the filter transfer function and the signal actually recorded.

Example of a Deconvolution Procedure

Upon carrying out the trial, calculations were made on 80 points, which represented about 120 ms.

The calculation interval was between the indices 512 (instant of cutoff, namely $t_0$) and 592 (namely $t_0+120$ ms).

The chosen algorithm was based on the principle of successive approximations consisting, as known per se, in minimizing a squared deviation. For further details, reference can, for example, be made to the publication "An Algorithm for least square estimation of non-linear parameters J. Soc. Indust. and Applied Math. 11. No. 2—MARQUARDT D. 1963".

In this particular case the general diagram of this algorithm was as follows:

1) Let Ao, Bo, Co, $\tau_0$ be the previously identified values of V(t) and $Ki_{ref}$=squared deviation between the linear component of the model obtained after identification and the linear component of the function to be deconvolved, which is of course of the same type as the postulated function V(t).

Thus generate the model $V(nT)=Ao(nT)+Bo+Co \cdot e^{(-nT/\tau_0)}$ in the calculation interval (T representing the sampling frequency) with $Ki_1$=squared deviation between the convolved function (namely [h(nT) * V(nT)], h(nT) being the response of the filter 11) and the function to be deconvolved.

2) Next calculate dC, such that if $V(nT)=Ao(nT)+Bo+(Co+dC) e^{(-nT/\tau_0)}$, we have: $dki=Ki_2-Ki_1<0$ with $Ki_2$=squared deviation between the convolution [h(nT) * V(nT)] and the function to be deconvolved, store dC, next $$C = Co - Ki_1 \times \frac{dC}{dKi}$$

3) Calculate $d\tau$, such that if: $V(nT)=Ao(nT)+Bo+Coe^{(-nT/\tau_0+d\tau)}$, we have: $dKi=Ki_2-Ki_1 <0$ with $Ki_2$=Squared deviation between [h(nT) 8 V(nT)] and the function to be deconvolved, Store $d\tau$ and the parameters of the model V(nT), next $$\tau = \tau_0 - Ki_1 \times \frac{d\tau}{dKi}$$

4) Next generate the model: $V(nT)=Ao(nT)+Bo+(Co+dC) e^{(-nT/\tau_0+d\tau)}$ with at each iteration, calculation of $Ki_3$=Squared deviation between [h(nT) * V(nT)] and the function to be deconvolved If the stopping criterion (for example squared deviation $<Ki_{ref}$) is attained, interrupt the iterations.

Otherwise recommence at (1) by modifying Co so that Co<next C and $\tau_0$<next $\tau$, until the stopping criterion is satisfied.

The table below shows the effectiveness of this method by successive approximations.

TABLE 3

| TRIALS | A | B | C | $\tau_1$ | U | Potential jump |
|---|---|---|---|---|---|---|
| 1 | −3 | 200 | 57 | 50 | 500 | 243 |
| 2 | −4 | 300 | 22 | 29 | 500 | 178 |
| 3 | −6 | 350 | 97 | 50 | 1000 | 553 |
| 4 | −10 | 800 | 202 | 100 | 1500 | 498 |

NB: Once again, only $C_1$ and $\tau_1$ have been considered.

In practice, a good choice of model and of initial parameters enables rapid convergence of the method to be obtained.

Having thus approximated a monotonic function representing what would be the monotonic variation in potential of the structure measured without analogue filter and with practically no interference, it then suffices to identify with this function, whose convolution has minimized the squared deviation, the ohmic drop and various electrochemical phenomena whose respective amplitudes give a picture of the electrochemical situation existing between the metal of the work and the ground at the moment of cutoff.

On this topic, it will be recalled that quantitative knowledge of the amplitudes and rates of change immediately after cutoff makes it possible to determine which electrochemical phenomena are involved when the work, on leaving the protective situation, changes to a corrosion situation.

Among the various electrochemical phenomena concerned, the following typical conditions will be noted in particular:

complete insulating coating=RC circuit $Fe/Fe^{++}$cell in an acid medium $Fe/Fe^{++}$cell in a sequestering medium $Fe/Fe^{++}$cell in a sulphide-containing medium combination of the three conditions above with the buffer-capacity parameter and the parameter $Ca^{++}$·/$CO_3H^-$, $H/H^+$cell under various conditions of pH, of buffer capacity and of accessibility related to the $Ca^{++}$·/$CO_3H^-$ parameter, $O_2$, $H_2O/OH^-$cell with various pHs, various concentrations and combination with the buffer-capacity and accessibility parameters.

combination of the above parameters with the form of the defects in insulating coating, and reduced to three cases: narrow pinhole, wide defect, porous coating.

By way of conclusion, it will again be noted that the method of processing the captured signals, used in the invention, groups into a single parameter all the phenomena which are markedly faster than the filter itself and into a single set of two parameters, (amplitude and time constant), all the phenomena whose time constant is close to that of the filtering unit.

However, experience shows that in practice this always enables the relevant phenomena to be identified.

Two reasons can be advanced for this:

under the practical conditions of protection in the ground, there is actually a single chemical phenomenon which is faster than the filter itself: depolarization by sulphides, and furthermore, the chemical phenomena are characterized here not only by their amplitude and their time constant, but also by the level of potential at which they intervene, these depolarization phenomena which are observed during the few seconds following cutoff, being decomposed, by virtue of the invention, into a restricted number of physical or physicochemical manifestations which are independent, monotonic and separated in level of potential and in time.

What is claimed is:

1. Method for obtaining information on a changeover time of a voltage between a reference electrode and a metal structure, both in contact with an electrolytic medium, said structure being protected against corrosion by an anodic or cathodic protective electrical current circulating between said structure and a counter-electrode in contact with said medium, said method comprising the steps:

(a) interrupting the circulation of said protective current for a time interval;
   (b) during said time interval, recording said voltage between said structure and said reference electrode;
   (c) filtering said recorded voltage in an analog filter having a response, in order to obtain filtered signals;
   (d) smoothing said filtered signals by substituting them with values corresponding to a postulated function of a continuous and monotonic type (V(t)); and
   (e) mathematically reconstructing, from said postulated function a changeover time of the voltage between said structure and said reference electrode, such that said voltage is free of filtering and electrical interference.

2. Method according to claim 1 further including, during step (e):

conducting a convolution transformation between said response of the analog filter and the postulated function V(t) for obtaining a convolution result; and comparing said convolution result with said postulated function;
   repeating the conducting step, while changing said function until a function is obtained whose convolution result approximates a predetermined deviation of said postulated function;
   and regarding said determined function as corresponding to said changeover time of said voltage between the structure and the reference electrode during the time interval in which said protective current is interrupted.

3. Method according to claim 1 wherein said postulated function V(t) corresponds to a change in the voltage between the structure and the reference electrode as a function of time, said change corresponding to a voltage jump followed by a sum of at least an exponential variable and a polynomal variable.

4. Method according to claim 1 wherein said postulated function is of the type $V(t) = At + B + C_1 e^{-t/\gamma_1} + C_2 e^{-t/\gamma_2}$; $A$, $B$, $C_1$, $C_2$, $\gamma_1$, $\gamma_2$, being constants having the substitution values of step (d).

5. Method according to claim 2 wherein said determined function whose convolution result approximates the deviation of said postulated function (V(t)) is regarded as said changeover time of the voltage between said structure and said reference electrode, during said interruption of current, by identifying said determined function with depolarization phenomena existing during the said interruption of current.

6. Method according to claim 1 comprising, during step (d), determining the values to be substituted for said captured filtered signals by a least squares method.

7. Method according to claim 2 wherein said postulated function and said convolution result from the convolution transformation between the response of the analog filter and said successive predetermined functions of the same type as said postulated function, made to converge by a method of successive approximations.

8. Method according to claim 1 further comprising the following steps:

(f) re-establishing the circulation of said protective current during a new specified time interval;
   (g) repeating steps (b) and (c),
   (h) statistically calculating an average value of said captured signals to step (d);
   (i) and, supplying to a display unit information corresponding to signals and to said mathematical reconstruction undertaken during step (e).

9. Method for obtaining information on a changeover time of a voltage between a reference electrode and a metal structure, both being in contact with an electrolytic medium, said structure being protected against corrosion by an anodic or cathodic protective electrical current circulating between said structure and a counter-electrode in contact with said medium, said method comprising the steps:

(a) interrupting the circulation of said protective current for a time interval;
   (b) during said time interval, recording said voltage between said structure and said reference electrode;
   (c) filtering said recorded voltage in an analog filter having a response, in order to obtain filtered signals;
   (d) smoothing said filtered signals by substituting them with identification values corresponding to a postulated function of a type $V(t) = At + B + C_1 e^{-t/\gamma_1} + C_2 e^{-t/\gamma_2}$; $A$, $B$, $C_1$, $C_2$, $\gamma_1$, $\gamma_2$, being constants corresponding to said identification values;
   (e) performing a convolution transformation between said response of the analog filter and a given function of the same type as said postulated function V(t), for obtaining a convolution result, and comparing said convolution result with said postulated function;
   (f) repeating said step (e), while changing said given function until obtaining a determined function whose convolution result approximates a deviation of said postulated function;
   (g) and regarding said determined function as corresponding to a changeover time of said voltage between the structure and the reference electrode during the time interval in which said protective current is interrupted.

* * * * *

UNITED STATES PATENT AND TRADEMARK OFFICE
CERTIFICATE OF CORRECTION

PATENT NO. : 5,318,678
DATED : June 7, 1994
INVENTOR(S) : Pierre Callot

It is certified that error appears in the above-indentified patent and that said Letters Patent is hereby corrected as shown below:

Column 7, line 61, replace "h(nT) 8 V (nT)" with --h(nT) * V (nT)--.

Column 10, line 1, replace "$e^{-t/\gamma 1} + C_2^{-t/\gamma 2}$; A, B, $C_1$, $C_2$, $\gamma_1$, $\gamma_2$," with --$e^{-t/\tau 1} + C_2 e^{-t/\tau 2}$; A, B, $C_1$, $C_2$, $\tau_1$, $\tau_2$--.

Column 10, line 49, replace "$e^{-t/\gamma 1} + C_2 e^{-t/\gamma 2}$; A, B, $C_1$, $C_2$, $\gamma_1$, $\gamma_2$," with --$e^{-t/\tau 1} + C_2 e^{-t/\tau 2}$; A, B, $C_1$, $C_2$, $\tau_1$, $\tau_2$--.

Signed and Sealed this

Twenty-third Day of May, 1995

Attest:

BRUCE LEHMAN

*Attesting Officer*   *Commissioner of Patents and Trademarks*